United States Patent [19]

Payne et al.

[11] Patent Number: 4,525,203
[45] Date of Patent: Jun. 25, 1985

[54] ((3,4,5,6-TETRAHYDRO-2H-PYRAN-2-YL)METHOXY)OXABICYCLOALKANE HERBICIDES

[75] Inventors: George B. Payne, Modesto; James E. Powell, Ripon, both of Calif.

[73] Assignee: Shell Oil Company, Houston, Tex.

[21] Appl. No.: 621,012

[22] Filed: Jun. 15, 1984

[51] Int. Cl.³ .................. A01N 43/00; C07D 407/00; C07D 315/00
[52] U.S. Cl. ........................ 71/88; 549/273; 549/397; 549/414
[58] Field of Search .............. 549/414, 273, 397; 71/88

[56] References Cited

U.S. PATENT DOCUMENTS 2,576,901 11/1951 Jong .................................. 549/273

FOREIGN PATENT DOCUMENTS 81893 6/1983 European Pat. Off. .

Primary Examiner—Ethel G. Love

[57] ABSTRACT

Compounds of the formula

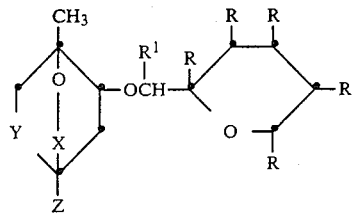

wherein X is a single bond or $-C(CH_3)_2$; Y is a single bond or $-CH_2-$ with the proviso that both X and Y are not a single bond, and Z is H or alkyl; each R is H, hydroxy, oxo, methylene, alkyl or alkoxy, or one pair of adjacent R groups form a carbon-carbon bond; and $R^1$ is H or alkyl, are useful as herbicides or plant growth regulators.

10 Claims, No Drawings

((3,4,5,6-TETRAHYDRO-2H-PYRAN-2-YL)METHOXY)OXABICYCLOALKANE HERBICIDES

BACKGROUND OF THE INVENTION

1. Field of the Invention

The present invention relates to novel ((3,4,5,6-tetrahydro-2H-pyran-2-yl)methoxy)oxabicycloalkane derivatives, their use for controlling plant growth and as herbicides and to herbicidal and plant growth regulating compositions containing these novel derivatives.

2. Summary of the Invention

The present invention is directed to novel ((3,4,5,6-tetrahydro-2H-pyran-2-yl)methoxy)oxabicycloalkanes of the formula 1

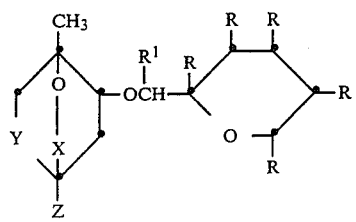

wherein X is a single bond or —C(CH$_3$)$_2$, Y is a single bond or —CH$_2$— with the proviso that both X and Y are not a single bond; Z is H, or an alkyl group containing 1 to 4 carbon atoms; each R independently is a hydrogen atom, a hydroxy group, an oxo group, a methylene group, or an alkyl or alkoxy group in which the alkyl portion contains from 1 to 6 carbon atoms or one pair of adjacent R groups form a carbon-carbon bond; and R$^1$ is a hydrogen atom or an alkyl group containing 1 to 6 carbon atoms. The compounds are useful as plant growth regulators or herbicides and intermediates therefor.

Non-limiting embodiments of the compounds of formula 1 of the present invention include
6-((3,4,5,6-tetrahydro-2H-pyran-2-yl)methoxy)-1,3,3-trimethyl-2-oxabicyclo[2.2.2]octane,
6-((3,4,5,6-tetrahydro-2H-pyran-2-yl)methoxy)-1,3,3-trimethyl-4-ethyl-2-oxabicyclo[2.2.2]octane,
2-((3,4,5,6-tetrahydro-2H-pyran-2-yl)methoxy-1-methyl-4-ethyl-7-oxabicyclo[2.2.1]heptane,
2-((3,4,5,6-tetrahydro-2H-pyran-2-yl)methoxy)-1-methyl-7-oxabicyclo[2.2.1]heptane,
2-((3,4,5,6-tetrahydro-2H-pyran-2-yl)methoxy)-1-methyl-4-(1-methylethyl)-7-oxabicyclo[2.2.1]heptane,
6-((3,4,5,6-tetrahydro-2H-pyran-2-yl)methoxy)-1,3,3-trimethyl-2-oxabicyclo[2.2.1]heptane, and the like.

The compounds of formula 1 exhibit geometrical and optical isomerism and can be prepared in geometrical and/or optically-active forms, and as racemates. The various individual optically and geometrical combinations of the materials of the invention usually have some different herbicidal properties. The present invention contemplates all the herbicidally active forms resulting from synthesis and deliberately created mixtures. Some of the ((3,4,5,6-tetrahydro-2H-pyran-2-yl)methyl ether compounds of the invention also have good photostability relative to the corresponding benzyl ethers as well as higher vapor pressure and increased hydrophilicity.

One embodiment of the present invention is directed to compounds of formula 1 of the invention wherein (1) X is a single bond, Y is —CH$_2$— and Z is a hydrogen atom or a 1-methylethyl group or (2) X is —C(CH$_3$)$_2$—, and Z is a hydrogen atom. Preferably, when X is a single bond then Z is a 1-methylethyl group.

In another embodiment of the invention, each R independently is a hydrogen atom or an alkyl or an alkoxy group containing 1 or 2 carbon atoms and R$^1$ is a hydrogen atom or methyl group. Preferably, each R independently is a hydrogen atom or a methyl group and R$^1$ is a hydrogen atom.

The compounds of the invention described by formula 1 are prepared by treating an appropriately substituted oxabicycloalkanol with a compound of the formula

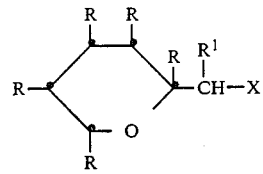

in which X is a halogen atom, such as bromine, chlorine or iodine, or is a hydrocarbylsulfonyloxy group, e.g. a mesyloxy, tosyloxy group or the like, preferably in the presence of a strong base and an inert diluent. The strong base is suitably an alkali metal hydride, hydroxide or carbonate, including, for example, sodium hydride, sodium hydroxide, potassium carbonate and the like. Inert diluents are suitably organic solvents, such as ethers, aromatic hydrocarbons, chlorinated hydrocarbons and the like, including, for example, diethyl ether, tetrahydrofuran, dimethyl sulfoxide, toluene, methylene chloride and the like. The reaction is usually carried out under normal pressures and ambient temperatures. Suitable temperatures for the reaction are from about 0° to about 120° C., preferably from about 20° to about 100° C. The product ethers are recovered and isolated by conventional techniques.

The oxabicycloalkanol reactants are obtained generally by one or more of the following routes: directly by (a) epoxidation-cyclization of unsaturated cyclic alcohols, with or without isolation of epoxy alcohol intermediates; and indirectly by (b) Diels-Alder reactions of furans with dienophiles or (c) Birch reduction, etc.

Detailed routes are described below for the different ring systems.

In (a), the epoxidation-cyclization of unsaturated cyclic alcohols involves treatment in an inert solvent by an oxidizing agent followed by an acid. The alcohols are either (i) cycloalk-3-en-1-ols, or (ii) cycloalk-3-ene-1-methanols. The cycloalk-3-en-1-ols, useful for preparing compounds of the invention, are prepared from 1-oxaspiro(2.5)oct-5-enes: by reduction; by rearrangement and reduction of 1-oxaspiro(2.5) oct-5-enes; by reduction of cycloalk-3-en-1-ones; by treatment of cycloalk-3-en-1-ones with a Grignard reagent; by dealkylating or hydrolyzing, respectively, Diels-Alder adducts of vinyl ethers or esters prepared from dienes, such as isoprene, and vinyl ether or ester dienophiles in which the alpha-position of the vinyl group is substituted by alkyl, CO$_2$R$^8$, or CON(R$^8$)$_2$. The cycloalk-3-ene-1-methanols are (1) alpha-terpineol; (2) Diels-Alder adducts of allylic alcohols; or (3) products obtained from Diels-Alder adducts of alpha-beta unsaturated carbonyl compounds, such as acrylates, crotonates, acrolein or alkyl(methyl) vinyl ketone, by reduction or treatment with a Grignard reagent.

In (b), the Diels-Alder type adducts of furans with dienophiles may require vigorous reaction conditions, including high pressure and low temperature, for example, as described in Dauben, W. G. et al., *J. Amer. Chem. Soc.*, 102, page 6894 (1980). When the dienophile is nitroethylene, the resulting product is hydrogenated, then oxidized to the ketone and reduced to the corresponding alcohol, e.g. by treatment with a hydride or metal. When this alcohol has the endo form, it can be epimerized with base or aluminum isopropoxide in the presence of a ketone to the corresponding exo alcohol.

Endo- and exo-oxabicycloalkanol intermediates can be separated by conventional methods, such as crystallization, chromatography and the like, and the geometric forms can be resolved by classical resolution methods to give a substantially pure single, optically-active isomer.

Non-limiting illustrations of the preparation of representative Compounds of the Invention follow.

In one embodiment, compounds having the formula I

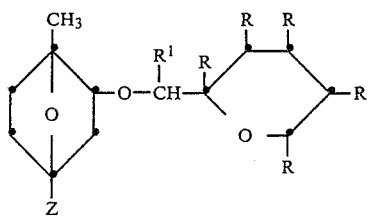

wherein Z has the above meaning can be prepared from 7-oxabicyclo[2.2.1]-heptan-2-ols obtained from (1) cyclohex-3-en-1-ols, by epoxidation-cyclization, or (2) Diels-Alder adducts of furans, such as 2,5-dimethylfuran, with dienophiles, such as nitroethylene, as described below.

The epoxidation of cyclohex-3-en-1-ols into the corresponding epoxy-alcohol is effected by action of an oxidizing agent, particularly a peroxide, such as m-chloroperbenzoic acid, peracetic acid, tert-butyl hydroperoxide (TBHP) or equivalent peroxide reagents. The oxidation to cis-alcohols with TBHP is conducted in the presence of an appropriate transition metal catalyst, e.g. vanadium. Preferably, the complex is an organic complex, for example, with beta-diketones, o-hydroxybenzaldehydes or o-hydroxybenzophenones and particularly with acetylacetone, for example, vanadium(IV) bis(2,4-pentanedionate)oxide is preferred. The reaction is suitably conducted in the presence of an inert solvent such as chlorinated hydrocarbons, ethers, hydrocarbons or the like. Suitable chlorinated hydrocarbons contain from 1 to 4 chlorine atoms in combination with an alkane chain containing from 1 to 4 carbon atoms or a benzene ring, for example, carbon tetrachloride, chloroform, dichloromethane, chlorobenzene and 1,2- or 1,3-dichlorobenzene and the like. Ethers are generally those containing from 4 to 6 carbon, for example, diethyl ether, methyl tert-butyl ether and diisopropyl ether. Tetrahydrofuran and dioxane are also useful. Suitable alkanes contain from 5 to 10 carbon atoms, for example, n-pentane, n-hexane, n-heptane, n-octane, n-nonane, n-decane and their isomers. Petroleum fractions rich in alkanes are also suitable. Petroleum ether is also suitable. Cyclohexane and methylcyclohexane are examples of useful cycloalkane solvents containing from 6 to 8 carbon atoms. Suitable aromatic hydrocarbon solvents contain from 6 to 10 carbon atoms, for example, benzene, toluene, o-, m-, and p-xylene, the trimethylbenzenes, p-ethyltoluene and the like. The reaction is conducted at temperatures conveniently in the range of from about −10° C. to about 50° C. or slightly above. Generally, the temperature is from about −5° C. to about 40° C., preferably from about 10° C. to about 30° C. The molar ratio of reactants can vary. Generally, a molar ratio of cyclohex-3-en-1-ol to oxidizing agent is from about 0.8 to about 1.0. The reaction is usually conducted by forming a mixture of the alcohol and oxidizing agent, preferably while agitating the reaction mixture, e.g. by stirring, and maintaining the desired reaction temperature. The resulting cis-epoxy-alcohol may be purified or converted without isolation into the 2-exo-hydroxy-7-oxabicyclo[2.2.1]-heptane by cyclization as described below.

The cyclization (ring closure) step surprisingly gave a high yield of product having the exo-hydroxy configuration in the resulting 7-oxabicyclo[2.2.1]heptan-2-ol. Many acids will catalyze this reaction, but a relatively strong acid such as sulfuric or sulfonic acids are suitable. Preferably, the acid is methanesulfonic acid or an arylsulfonic acid, such as p-toluenesulfonic, benzenesulfonic acids, or the like. Of these, p-toluenesulfonic acid is preferred. The reaction is suitably conducted by adding the acid to the epoxy-alcohol contained in an inert solvent of the type previously described for use in the preparation of the epoxy-alcohol. The reaction is conducted at a temperature conveniently in the range of from about 0° C. to about 50° C. or slightly above. Generally, the temperature is from about 5° C. to about 40° C., preferably from about 10° C. to about 30° C. The molar ratio of reactants can vary. Generally, the molar ratio of acid to epoxy-alcohol is from about 0.01 to about 0.10, and preferably from about 0.02 to about 0.04.

Thus, a 1,4-disubstituted-3-cyclohexen-1-ol is converted mainly to 2-exo-hydroxy-1,4-disubstituted-7-oxabicyclo[2.2.1]heptane by treating it with an oxidizing agent, such as tert-butyl hydroperoxide, or m-chloroperbenzoic acid, and then a strong acid, such as p-toluenesulfonic acid. Especially useful for obtaining a 2-exo-hydroxy-1,4-disubstituted-7-oxabicyclo[2.2.1]heptane is treatment of the corresponding 3-cyclohexen-1-ol with tert-butyl hydroperoxide and vanadium-(IV) bis(2,4-pentanedionate)oxide as catalyst in methylene chloride followed by treatment of the intermediate epoxide, preferably in situ, with a sulfonic acid, particularly p-toluenesulfonic acid. Also, acid present during the epoxidation step produces the desired product.

The epoxidation-cyclization is disclosed and claimed in co-pending U.S. patent application Ser. No. 331,095, filed Dec. 16, 1981, and Ser. No. 414,548, filed Sept. 8, 1982, both abandoned and in Ser. No. 559,512, filed Dec. 8, 1983.

In situations where the endo form is desired, it can be obtained by oxidation of the 2-exo-hydroxy compound to the corresponding ketone followed by reduction of the ketone with sodium borohydride.

The 3-cyclohexen-1-ols useful for the preparation of Compound I can also be synthesized as described below or obtained from natural source (which offer the advantage of optically-active materials).

(a) where Z is 1-methylethyl, the starting compound is terpinen-4-ol, which occurs naturally. Terpinen-4-ol is converted to 2-exo-hydroxy-1-methyl-4-(1-methylethyl)-7-oxabicyclo[2.2.1]heptane by treatment with an oxidizing agent, for example, a peroxide such as m- chloroperbenzoic acid, peracetic acid or tert-butyl hydroperoxide, in an inert solvent. The optical configuration of terpinen-4-ol is retained in the reaction. Thus, (±), (−) or (+) 2-exo-hydroxy-1-methyl-4-(1-methylethyl)-7-oxabicyclo[2.2.1]heptane can be obtained. 2-endo-Hydroxy-1-methyl-4-(1-methylethyl)-7-oxabicyclo[2.2.1]heptane is known from Garside et al., *J. Chem. Soc.*, page 716–721 (1969). 2-exo- and endo-Hydroxy-1-methyl-4-(1-methylethyl)-7-oxabicyclo[2.2.1]heptanes are converted to the ethers of the invention as described above. Although terpinen-4-ol occurs in nature in optically active and racemic forms, it can also be prepared by epoxidation of terpinolene, e.g. with peracetic acid in methylene chloride, followed by reduction of the epoxide, e.g. with sodium diethylaluminum hydride in tetrahydrofuran.

(b) Preparation of 3-cyclohexen-1-ols can be effected from p-substituted phenols in which the substituent group corresponds to methyl in the formula I of the invention by procedures of the literature for the Birch-type reduction of derivatives of benzene, many of which are detailed in Rodd's Chemistry of Carbon Compounds, Second Edition, Vol. II, Part B, pages 1–4 (1968). In an example, para-cresol is first methylated to protect the hydroxy group yielding the corresponding p-methylanisole. This p-methylanisole is treated with a reducing agent such as lithium-ammonia or sodium-ammonia and the resulting product is hydrolyzed to yield the corresponding 4-methyl-3-cyclohexen-1-one. Treatment of this ketone with an appropriate organometallic (Grignard) reagent, ZMgBr or ZLi in which Z corresponds to that in the formula I of the invention and is alkyl, e.g. at 20°–60° C. in the presence of anhydrous ethers, yields the desired 1,4-disubstituted-3-cyclohexen-1-ol intermediate. The 4-methyl-3-cyclohexen-1-one can also be reduced, e.g. by hydrides, to the corresponding 3-cyclohexen-1-ol unsubstituted in position-1.

The 2-hydroxy-7-oxabicyclo[2.2.1]heptanes useful as precursors of compounds of the invention can also be prepared from Diels-Alder adducts of suitably-substituted furans, as dienes, and dienophiles. For example, 2,5-dimethylfuran adds readily to nitroethylene to give 1,4-dimethyl-2-nitrobicyclo[2.2.1]hept-5-ene. Similar adducts can be prepared from 2,5-dialkylfurans and dienophiles such as acrolein and acrylate esters.

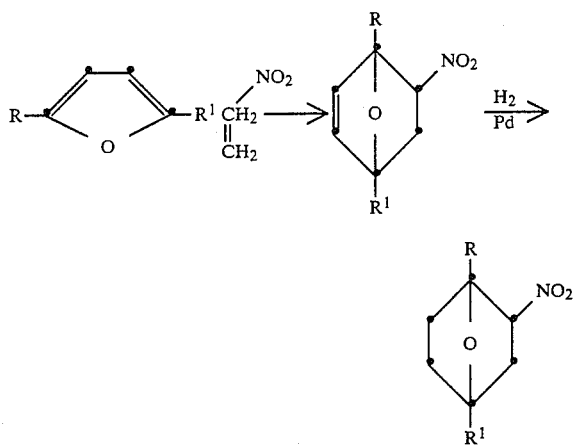

Severe reaction conditions including low temperature and high pressure may be required for some Diels-Alder reactions of substituted furans, for example, as described in Dauben, W. G. et al., *J. Am. Chem. Soc.*, 102, page 6894 (1980). Hydrogenation and treatment of the nitro compound with a strong base such as potassium hydroxide, followed by an oxidizing agent, such as potassium permanganate, singlet oxygen, aqueous $TiCl_3$, tert-butyl hydroperoxide in the presence of vanadium(IV) bis(2,4-pentanedionate)oxide or the like, affords the 1,4-disubstituted bicyclo[2.2.1]heptan-2-one. Reduction with a hydride or metal converts the ketone to the desired 2-hydroxybicyclo[2.2.1]heptane useful for preparation of compounds of the invention by aralkylation. Where the hydroxy group is in the endo orientation, epimerization to the more desirable 2-exo-hydroxy stereoisomer can be effected by treatment with a base, such as sodium hydroxide, or aluminum alkoxide in the presence of a ketone, preferably the corresponding ketone.

The materials of formula I that have the $RCH_2O$ group (in which R is e.g. a (3,4,5,6-tetrahydro-2H-pyran-2-yl) group exo (formula Ia below) with respect to the oxygen-containing bridge are usually more herbicidally active than the endo form (formula Ib below) or the exo-endo mixture and are preferred.

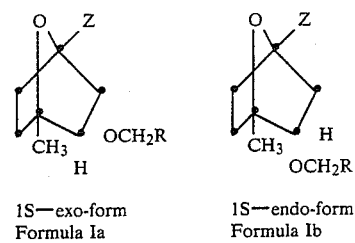

1S—exo-form  1S—endo-form
Formula Ia  Formula Ib

The compounds of formula Ia and Ib have the 1S absolute configuration shown above. Such compounds of the subclass of formula Ia of the invention that correspond in configuration are preferred.

When an isomer or a mixture of isomers other than racemic mixtures is used substantially free of all other possible isomers, they are usually at least about 70% pure, although a purity above about 80% is preferable and a purity above about 95% is highly desirable. This invention contemplates all of the herbicidally active isomers, as well as any mixtures of isomers resulting from the synthesis methods used, and deliberately created mixtures.

In another embodiment of the invention, the compounds having the formula II

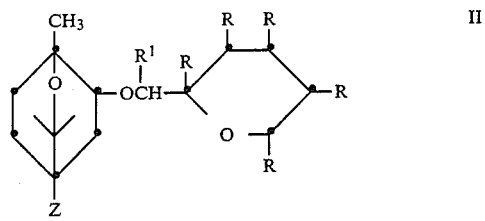

wherein Z has the above meaning, can be prepared from 2-oxabicyclo[2.2.2]heptan-6-ols, made from (1) terpenes, such as alpha-terpineol or (2) Diels-Alder adducts of suitably substituted butadienes and dienophiles containing an oxygen function, as illustrated below. For example, (1) the compound is obtained from naturally occuring terpenes. Most elementarily, alpha-pinene is treated with aqueous acid to form alpha-terpineol, itself a naturally occuring material. alpha-Terpineol, either in racemic form or completely or partially optically active form, is oxidized, for example, with a peroxide such as hydrogen peroxide or m-chloroperbenzoic acid in a suitable solvent like methylene chloride, to yield a major amount of 1,3,3-trimethyl-2-oxabicyclo[2.2.2]octan-6-exo-ol. Oxidation of this alcohol, e.g. with N-bromoacetamide in aqueous acetone at 5° C., gives 1,3,3-trimethyl-2-oxabicyclo[2.2.2]octan-6-one. Subsequent reduction of this ketone, for example with sodium borohydride in tert-butanol, yields a mixture of alcohols predominant in the endo isomer. Conversion to the ether of formula II of the Invention follows the earlier described procedures with retention of configuration.

(2) Diels-Alder adducts are formed from suitable, readily available dienophiles including an acrylate ester, acrolein, methacrolein, methyl vinyl ketone, allyl alcohol, a crotonate ester and the like. The diene component is isoprene, 2,3-dimethylbutadiene and the like. For example, the Diels-Alder adducts IIa are prepared by treating the portion of the compound of formula IIa above the dotted line

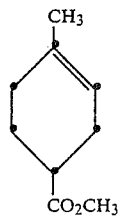

IIa with a dienophile (methyl acrylate) corresponding to the portion of the compound of formula IIa below the dotted line. Many such reactions are detailed in Rodd's Chemistry of Carbon Compounds, Second Edition, Vol II, Part B, pages 5–6 (1968). Treatment of IIa with the appropriate Grignard reagent (e.g. methyl magnesium bromide, ethyl magnesium bromide or the like) gives an alpha,alpha,4-trimethyl-cyclohexene-1-methanol of formula IIb below.

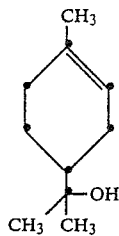

IIb

Alcohol IIb is oxidized, for example, with a peroxide, such as hydrogen peroxide or m-chloroperbenzoic acid, in a suitable solvent, such as methylene chloride, preferably in the presence of a strong acid, to yield a major amount of 1,3,3-trialkyl-2-oxabicyclo[2.2.2]octan-6-exo-ol. This exo form can be converted, if desired, into an endo-rich or substantially pure endo form. First, oxidation to the corresponding ketone, 1,3,3-trialkyl-2-oxabicyclo[2.2.2]octan-6-one, is effected with a suitable oxidizing agent. For example, the exo form is combined with oxalyl chloride and dimethyl sulfoxide in methylene chloride followed by addition of triethylamine. Then, the resulting ketone is converted into the endo-alcohol by reduction. For example, the ketone in a mixture of dimethoxyethane and tert-butanol is treated with sodium borohydride. Classical resolution can be applied to the 1,3,3-trialkyl-2-oxabicyclo[2.2.2]octan-6-ols to give substantially pure individual optical forms. The 1,3,3-trialkyl-2-oxabicyclo[2.2.2]octan-6-ols are converted into the desired ethers of the Invention, with retention of configuration, by treatment with a tetrahydrofuran-2-ylmethyl halide or sulfonate in which X is a halogen atom or hydrocarbylsulfonyloxy group, such as chlorine, mesyloxy or tolyloxy. This reaction is carried out, preferably in the presence of a base, such as sodium hydride, and, if desired, an inert solvent, such as N,N-dimethylacetamide, N,N-dimethylformamide, benzene, toluene or the like. The compounds of the invention can be recovered and purified by conventional techniques.

The materials of formula II that have the $RCH_2O$ group (in which R is, e.g. a (3,4,5,6-tetrahydro-2H-pyran-2-yl) group endo (formula IIc below) are usually more herbicidally active than the exo form (formula IId below) or the endo-exo mixture and are preferred.

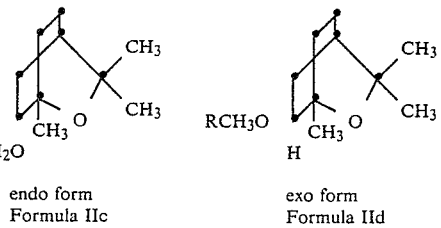

endo form
Formula IIc exo form
Formula IId

The compounds of formula IIc and IId have the 1S absolute configuration shown above. Such compounds of the subclass of formula IIc of the invention that correspond in configuration are preferred. When an isomer or a mixture of isomers other than a racemic mixture is used substantially free of all other possible isomers, they are usually about 70% pure, although a purity above about 80% is preferable and a purity above about 95% is highly desirable. This invention contemplates all of the herbicidally active isomers, as well as any mixtures resulting from the synthesis methods used, and deliberately created mixtures.

In another embodiment of the invention, the compounds having the formula III

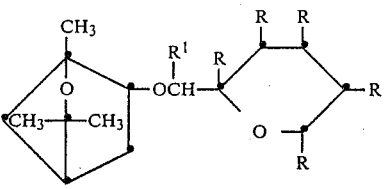

III in which R and $R^1$ have the above meanings, can be prepared by condensation of 1,4-dibromo-2-methyl-2-butene with an alkyl acetoacetate, in the presence of base, followed by thermolysis of the isopropenyl acetyl cyclopropanecarboxylate intermediate to a cyclopentene carboxylate, which is hydrolyzed and decarboxylated to the corresponding ketone. Treatment of the ketone with a Grignard reagent, methyl magnesium bromide, yields the corresponding alcohol derivative. This alcohol is epoxidized and cyclized to an exo-2-oxabicyclo[2.2.1]heptan-6-ol. This exo-alcohol can be oxidized to the corresponding ketone followed by reduction to a corresponding endo-2-oxabicyclo[2.2.1]heptan-6-ol as described for the compounds of formula IIp above. The alcohol is treated with a tetrahydropyran-2-ylmethyl halide or sulfonate to yield the desired ether IIIp. An example of one alternative method is the condensation of a 1,4-dibromo-2-methyl-2-butene with a malonic acid dialkyl ester, again using base, followed by thermolysis. The resulting cyclopentene derivative is treated with, e.g., sodium chloride in dimethyl sulfoxide to eliminate one of the ester functional groups. Treatment of the resulting mono ester with the Grignard reagent, methyl magnesium bromide, yields the alcohol derivative previously described in the first methodology. See, also, Spurlock et al., Chemical Abstracts, 76:153024e (1972) for preparation of a 2-oxabicyclo[2.2.1]heptan-6-ol.

The materials of formula III that have the RCH₂O group (in which R is, e.g. (3,4,5,6-tetrahydro-2H-pyran-2-yl) endo (formula IIId below) are usually more herbicidally active than the exo form (formula IIIc below) or the endo-exo mixture and are preferred.

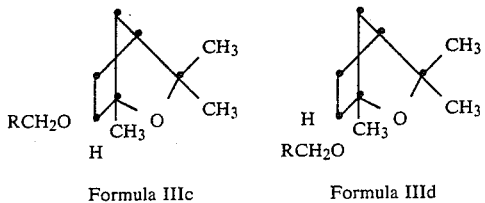

Formula IIIc          Formula IIId

These compounds of formula IIIc and IIId have the 1S absolute configuration shown above. Such compounds of the formula IIId of the invention are preferred. When an isomer or a mixture of isomers other than a racemic mixture is used substantially free of all other possible isomers, they are usually about 70% pure, although purity above 80% is preferred and a purity above about 95% is highly desirable. This invention contemplates all of the herbicidally active isomers, as well as any mixtures resulting from the synthesis methods used, and deliberately created mixtures.

The (3,4,5,6-tetrahydro-2H-pyran-2-yl)methanol derivatives R—CH₂X in which X is a halogen atom, or hydrocarbylsulfonyloxy group and R is the 2H-pyran moiety defined above in formula 1 are generally known in the art and are readily prepared from the (3,4,5,6-tetrahydro-2H-pyran-2-yl)methanols, by conventional methods known in the art for preparing halides and sulfonates of alcohols. For example, the tosylate is described in R. J. Palmer et al., *J. Amer. Chem. Soc.*, 102 (27) pages 7888-92 (1980) as well as its preparation. The (3,4,5,6-tetrahydro-2H-pyran-2-yl)methanols are known materials or can be prepared by literature methods including application of the methods of G. Buchi and J. E. Powell, *J. Amer. Chem. Soc.*, 92, 3126 (1970); E. L. Eliel, M. Manoharan, K. M. Pietrusiewicz, K. D. Hargrave, *Org. Magn. Res.*, 21, 94 (1983); E. L. Eliel, K. D. Hargrave, K. M. Pietrusiewicz, M. Manoharan, *J. Amer. Chem. Soc.*, 104, 3635 (1982) and J. Jurczak and M. Tkacz, *J. Org. Chem.*, 44, 3347 (1979). For example, the alkylated (3,4,5,6-tetrahydro-2H-pyran-2-yl)methanols and the (3,4-dihydro-2H-pyran-2-yl)methanols are prepared by forming adducts from simple, readily available, unsaturated and oxygenated conventional materials, e.g. acrolein, methyl vinyl ketone, isoprene, diethyl oxomalonate and the like. Thus, known acrolein dimer, methyl vinyl ketone dimer and isoprene diethyl oxomalonate adduct and the like, are useful pyranyl derivative intermediates containing a functional carbonyl, or carboxylic acid or ester group which is further derivatized by one or more conventional techniques of, e.g. (a) imine formation, for example, using t-butylamine in an inert solvent followed by a Grignard reagent and methyl iodide; (b) carbonyl formation, for example, by treating an imine with aqueous acetic acid; (c) decarboxylation, for example, by treating a carboxylic acid ester substituent with hydrochloric acid; (d) reduction, for example, of a ring double bond by hydrogenation in the presence of a noble metal catalyst such as Pt/C, reduction of a carbonyl substituent to hydroxymethyl with sodium borohydride or reduction of a carboxylic acid substituent (optionally from hydrolysis of the corresponding ester) with lithium aluminum hydride, to obtain the desired 2H-pyran-2-methanol intermediate, which for convenience, is usually converted to their corresponding alkyl or aralkyl sulfonyloxy derivative for reaction with the desired oxabicycloalkanol to form an ether of formula 1.

A dihydro-2H-pyran-2-ylmethoxy ether of Formula 1 is an especially useful intermediate to the ethers of formula 1 in which R is, e.g. hydroxy, oxo, methylene, alkyl or alkoxy by use of conventional synthesis techniques. For example, (3,4-dihydro-2H-pyran-2-yl)methanol ether is treated with, e.g. borane in tetrahydrofuran followed by hydrogen peroxide and sodium hydroxide, to give the corresponding (3,4,5,6-tetrahydro-5-hydroxy-2H-pyran-2-yl)methanol ether. This hydroxy ether is treated with, e.g. oxalyl chloride in dimethyl sulfoxide, to obtain the corresponding (3,4,5,6-tetrahydro-2H-5-oxo-pyran-2-yl)methanol ether. This oxo ether is treated with, e.g. methyl triphenyl phosphonium bromide, to obtain the corresponding (3,4,5,6-tetrahydro-2H-5-methylene-pyran-2-yl)methanol ether. This ether is treated with, e.g. hydrogen in the presence of platinum oxide and ethyl acetate, to give the corresponding (3,4,5,6-tetrahydro-2H-5-methoxypyran-2-yl)methanol ether.

ILLUSTRATIVE EMBODIMENTS

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

EMBODIMENT 1

(±)-2-exo-Hydroxy-1-methyl-4-(1-methylethyl)-7-oxabicyclo[2.2.1]heptane

To a solution of 22.3 g of 85% m-chloroperbenzoic acid in 150 ml of methylene chloride was added over 40 minutes a solution of 15.4 g of (±)-terpinen-4-ol in 30 ml methylene chloride at a temperature of about 0° C. The reaction mixture was stirred for 20 hours at room temperature, then cooled to 5° C. A solid was filtered and rinsed with cold methylene chloride. The combined filtrates were washed successively with one-eighth saturated potassium carbonate, saturated sodium sulfite, and then water, dried and Claisen distilled to yield 8.9 of product, b.p. 109°–113° C. at 8 mm. Recrystallization of the solidified distillate from pentane gave 5.5 g of the desired product, m.p. 42°–58° C.

EMBODIMENT 2

(±)-2-exo-Hydroxy-1-methyl-4-(1-methylethyl)-7-oxabicyclo[2.2.1]heptane

To a solution of 30.8 g of (±)-terpinen-4-ol and 0.8 g of vanadium(IV) bis(2,4-pentanedionate) oxide in 300 ml of methylene chloride was added 22.0 g of 90% tert-butyl hydroperoxide. The resulting reaction, initially mildly exothermic, was held at reflux for 2 hours, to obtain the epoxide, then 0.8 g of p-toluenesulfonic acid in 10 ml of glyme was added. The resulting reaction mixture was refluxed for 1.5 hours, and cooled, and 0.8 g of anhydrous sodium acetate was added with stirring. After filtration, the filtrate was concentrated and Claisen distilled to give 28.4 g of the desired product, b.p. 80°–95° (2 mm).

EMBODIMENT 3

(3,4,5,6-Tetrahydro-2H-pyran-2-yl)methyl methanesulfonate

A stirred solution of 13.9 g of 3,4,5,6-tetrahydro-2H-pyran-2-methanol and 18.2 g of triethylamine in 250 ml of methylene chloride was cooled to −10° C. and 15.1 g of methansulfonyl chloride was added dropwise over 5 minutes while maintaining the temperature at −10° C. to 0° C. using a cooling bath. The bath was removed and the mixture was stirred for ½ hour while the temperature reached 16° C. The reaction mixture was washed successively with 150 ml of ice water, 150 ml of 10% hydrochloric acid solution, 150 ml of saturated sodium bicarbonate solution and 150 ml of saturated sodium chloride solution, then dried (MgSO$_4$) and evaporated under vacuum at 50° C. to give 23.7 g of a yellow oil, which was Claisen distilled to yield 19.7 g of the desired product; b.p. 110° C. (0.2 mm).

EMBODIMENT 4

(±)-2-exo-(3,4,5,6-tetrahydro-2H-pyran-2-yl)methoxy)-1-methyl-4-(1-methylethyl)-7-oxabicyclo[2.2.1]heptane To a solution of 5.1 g of (±)-2-exo-hydroxy-1-methyl-4-(1-methylethyl)-7-oxabicyclo[2.2.1]heptane and 2.5 ml of N,N-dimethylformamide was added as one portion 1.6 g of 50% sodium hydride (washed with n-hexane). The reaction mixture was stirred at room temperature for 1 hour and then at 80°–85° C. for ½ hour. The reaction mixture was cooled to room temperature and 6.4 g of tetrahydropyran-2-ylmethyl mesylate was added in one portion. The reaction mixture was stirred for one hour at room temperature and then three hours at 80° C. The reaction mixture was poured into 250 ml of water, and extracted successively with 100 ml and two 50 ml portions of methylene chloride. The resulting methylene chloride solution was washed with 250 ml of water, dried (MgSO$_4$) and evaporated to give 8.5 g of an amber oil. This crude oil was Claison distilled to yield 4.1 g of the desired product; b.p. 110°–111° C.

EMBODIMENT 5

3,4,5,6-Tetrahydro-6-methyl-2-(1-oxoethyl)-2H-pyran

A mixture of 23.5 g of methyl vinyl ketone dimer, 2.35 g of 5% palladium on charcoal and 250 ml of ethanol was reacted with hydrogen in a 500 ml Parr shaker apparatus at 55 psi of hydrogen for 16 hours. The catalyst was removed by filtration through a bed of celite and the solvents were stripped to leave 21.5 g of a pale yellow oil. This material was combined with 80.0 g of products of two similar preparations and Kugelrohr distilled at 1.5 mm Hg to give 72.2 g of the desired product as a colorless oil collected at 62°–65° C.

EMBODIMENT 6

Methyl 3,4,5,6-Tetrahydro-6-methyl-2H-pyran-2-carboxylate

To a solution of 48.0 g of sodium hydroxide in 420 ml of water was added dropwise at 0°–10° C. 23 ml of bromine followed by dropwise addition of 21.3 g of the ketone of Embodiment 5 above. During the last addition the orange "bromine" color changed to an opaque yellow. The reaction mixture was stirred at 10° C. for 15 minutes and at 55°–65° C. for ½ hour. The cooled mixture was extracted twice with 250 ml of methylene chloride and then acidified to pH 2.0 with concentrated sulfuric acid. After first saturating the aqueous mixtures with sodium sulfate, the product was extracted four times with 250 ml methylene chloride, and the combined extracts were dried (MgSO$_4$) and stripped to leave a yellow oil. This oil was immediately dissolved in 200 ml of methanol and 27.9 ml of chlorotrimethylsilane was added. The temperature rose to 35° C. and the solution was stirred overnight. The solvents and excess chlorotrimethylsilane was stripped off on a rotary evaporator to leave 14.2 g of a pale yellow oil. This oil was Kugelrohr distilled at 0.9 mm Hg to give 13.3 g of the desired product collected at 55°–70° C.

EMBODIMENT 7

3,4,5,6-Tetrahydro-6-methyl-2H-pyran-2-methanol

To a solution of 3.8 g of lithium aluminum hydride in 400 ml of anhydrous diethyl ether under nitrogen was added at a rate to cause gentle reflux of the ether a solution of 13.0 g of the ester of Embodiment 6 above in 5 ml of anhydrous diethyl ether. The reaction mixture was refluxed for 2 hours and stirred at room temperature three days. The mixture was cooled with an ice bath and 3.8 ml of water, 3.8 ml of 15% sodium hydroxide, and 11.4 ml of water were added successively. The resultant solid was removed by filtration and the filtrate was dried (MgSO$_4$) and stripped on a rotary evaporator to leave 9.8 g of a colorless oil. This oil was Kugelrohr distilled at 4.5 mm Hg to give 8.64 g of the desired product as a colorless oil collected at 58°–63° C.

EMBODIMENT 8

(3,4,5,6-Tetrahydro-6-methyl-2H-pyran-2-yl)methyl Methanesulfonate

To a solution of 8.1 g of the alcohol of Embodiment 7 above, cooled by a dry ice/acetate bath, was added via syringe 12.5 ml of triethylamine followed by 5.4 ml of freshly distilled mesyl chloride via syringe at −5° C. to 0° C. During the exothermic addition, a white precipitate formed. After stirring at 15°–20° C. for ½ hour, the reaction mixture was diluted with 80 ml of water and 80 ml of methylene chloride, which caused the solids to dissolve. The phases were separated and the methylene chloride layer was washed successively with 50 ml of cold 6N hydrochloric acid, 50 ml of saturated sodium bicarbonate solution and 50 ml of saturated sodium chloride solution, dried (MgSO$_4$) and concentrated in vacuo to leave 13.6 g of an orange oil. This oil was Kugelrohr distilled at 0.02 mm Hg to yield 12.2 g of a colorless oil collected at 75°–78° C.

EMBODIMENT 9

(±)-2-exo-(3,4,5,6-Tetrahydro-6-methyl-2H-pyran-2-yl)-methoxy)-1-methyl-4-(1-methylethyl)-7-oxabicyclo[2.2.1]-heptane A solution of 4.25 g of (±)-2-exo-hydroxy-1-methyl-4-(1-methylethyl)-7-oxabicyclo[2.2.1]heptane of Embodiment 2 above in 50 ml of dimethylacetamide was added dropwise and rapidly to a suspension of 1.44 g of 50% sodium hydride (hexane washed) in 50 ml of dimethylacetamide. The resulting mixture was stirred for 1 hour at 60° C. and then 6.2 g of the mesylate of Embodiment 8 above in 30 ml of dimethylacetamide was added dropwise at 20°–30° C. The reaction mixture was stirred at room temperature for 4 days and then heated at 45°–55° C. for 6 hours. The resulting mixture was diluted with 400 ml of water and extracted thrice with 400 ml of methylene chloride. The combined organic extracts were washed with 400 ml of saturated sodium chloride solution, dried ($MgSO_4$) and stripped on a rotary evaporator to give 7.3 g of a pale yellow oil. The oil was flashed on a silica gel column using 1:10 diethyl ether/hexane as solvent to give the desired product as a single fraction of 3.90 g of a pale yellow oil.

EMBODIMENT 10

Diethyl 3,6-Dihydro-4-methyl-2H-pyran-2,2-dicarboxylate

A mixture of 25.0 g of ethyl oxomalonate, 50 ml of isoprene, 80 mg of hydroquinone and 140 ml of acetonitrile were heated for 6 hours under nitrogen in a stainless steel bomb using an oil bath at 135° C. The reaction mixture was cooled overnight and the solvent evaporated. The resulting product was distilled at 120°–130° C. (0.7 mm Hg) to give 29.6 g of an oil, which was flash chromatographed on silica gel using 20% ethyl acetate in hexane as solvent. The resulting fractions 18–40 were evaporated and Kugelrohr distilled to give 26.45 g of the desired product as a mixture of regioisomers.

EMBODIMENT 11

Diethyl 3,4,5,6-Tetrahydro-4-methyl-2H-pyran-2,2-dicarboxylate

A mixture of 12.5 g of the ester of Embodiment 10 above and 1.25 g of 5% platinum on carbon and 130 ml of absolute ethanol in a 500 ml Parr bomb were hydrogenated at 50 psi for 3 hours. The hydrogenation reaction was repeated with 12.05 g of the ester, 1.20 g of Pt/C and 120 ml of ethanol at 50 psi overnight. The combined reaction mixtures were filtered through Celite and evaporated. The combined materials were Kugelrohr distilled at 115°–130° C. (0.05 mm Hg) to give 23.8 g of a clear, colorless oil. The oil was separated into three batches, which were each flash chromatographed on silica gel using 15% ethyl acetate in hexane as solvent. Typically, the desired product was recovered in fractions 45–65. The three batches of product were combined and Kugelrohr distilled at 75°–85° C. (0.01 mm Hg) to give 17.1 g of the desired product as a clear, colorless oil.

EMBODIMENT 12

3,4,5,6-Tetrahydro-4-methyl-2H-pyran-2-carboxylate

A mixture of 16.6 g of the ester of Embodiment 11 above and 250 ml of 6N hydrochloric acid was refluxed for one day. The aqueous reaction mixture was extracted six times with 200 ml of ether and the combined ether extracts were washed with 600 ml of sodium chloride solution, dried ($Na_2SO_4$), filtered and evaporated to leave 9.83 g of a clear, colorless oil which was Kugelrohr distilled at 100°–110° C. (5 mm Hg) to give 8.78 g of the desired product as a clear, colorless oil.

EMBODIMENT 13

3,4,5,6-Tetrahydro-4-methyl-2H-pyran-2-methanol

A 250 ml 3-neck roundbottom flask was equipped with a condenser and dropping funnel and dried under nitrogen. After cooling, 40 ml of anhydrous tetrahydrofuran was added followed by 1.95 g of lithium aluminum hydride, added portionwise. The reaction mixture was refluxed for one hour, cooled to room temperature and 8.10 g of the acid of Embodiment 12 above in 20 ml of tetrahydrofuran was added dropwise over 15 minutes. The reaction mixture was refluxed for two hours and then stirred at room temperature under nitrogen for 3 days. To this stirred solution, was carefully added successively 2 ml of water, 2 ml of 15% sodium hydroxide solution and 6 ml of water. The reaction mixture was stirred rapidly for one hour to coagulate the aluminum salts, filtered through Celite, washed 6 times with dried tetrahydrofuran, filtered and evaporated to leave 7.5 g of crude product, which was Kugelrohr distilled at 100°–110° C. (30 mm Hg) to give 6.87 g of the desired product as a clear, colorless oil.

EMBODIMENT 14

3,4,5,6-Tetrahydro-4-methyl-2H-pyran-2-methanol Methanesulfonate

To a −10° C. solution of 6.61 g of the alcohol of Embodiment 13 above in 250 ml of methylene chloride and 10.6 ml of triethylamine in a 500 ml 3-necked flask under nitrogen was added dropwise over 20 minutes, 4.3 ml of mesyl chloride. The reaction mixture was stirred at −10° C. for 1¼ hours. The reaction mixture was washed successively with 300 ml of ice water, 300 ml of cold 10% hydrochloric acid solution, 300 ml of saturated sodium bicarbonate solution and 300 ml of sodium chloride solution, dried ($MgSO_4$), filtered and evaporated at 25° C. on a rotary evaporator and under high vacuum for 0.5 hour to leave 10.2 g of th desired mesylate.

EMBODIMENT 15

(±)-2-exo-((3,4,5,6-Tetrahydro-4-methyl-2H-pyran-2-yl)-methoxy)-1-methyl-4-(1-methylethyl)-7-oxabicyclo[2.2.1]heptane A dry 500 ml 3-necked roundbottom flask under nitrogen was charged with 3.4 g sodium hydride (hexane washed) and 250 ml of dimethylformamide followed by 8.17 g of alcohol of Embodiment 2 above, with some foaming. The reaction mixture was heated with stirring to 80° C. for 1 hour, cooled to room temperature and 10.0 g of the mesylate of Embodiment 14 above, was added as one portion. The reaction mixture was stirred overnight at room temperature. The solvent was evaporated using high vacuum at 50° C. The remaining oil was dissolved in 400 ml of ether and washed with 400 ml of water. The resulting aqueous phase was washed twice with 400 ml of ether and the combined ether layers were washed with 600 ml of sodium chloride solution, dried ($Na_2SO_4$) and evaporated leaving 12.5 g of a brown oil, which was flash chromatographed from silica gel using 20% ethyl acetate in hexane as solvent to give the desired product as fractions 18–31. These fractions were evaporated and Kugelrohr distilled at 100°–110° C. (0.01 mm Hg) to give 4.33 g of the desired product as a clear, colorless oil.

EMBODIMENT 16

3,4-Dihydro-N-(1,1-dimethylethyl)-2H-pyran-2-methanimine

A solution of 323.0 g of acrolein dimer in 230 ml of anhydrous ethanol was added dropwise to a solution of 251 ml of t-butylamine in 250 ml of anhydrous ethanol at 25° C. over 2 hours. The reaction mixture was stirred at room temperature overnight. The solvents were stripped off on a rotary evaporator to leave 295.5 g of a yellow oil. This oil was vacuum distilled at 8 mm Hg to give 223 g of a colorless oil at 63°–67° C. and four fractions of colorless oil were collected as follows: 2.82 g at 45°–63° C., 181.27 g at 63°–66° C., 42.42 g at 66°–67° C. and 37.09 g at 67°–70° C., and were a mixture of isomers of the desired product.

EMBODIMENT 17

3,4-Dihydro-2-methyl-N-(1,1-dimethylethyl)-2H-pyran-2-methanimine

Ethyl magnesium bromide was prepared by charging a 3 liter flask with 800 ml of ether, 38.4 g of magnesium turnings, a crystal of iodide followed by dropwise addition of 172.1 g of ethyl bromide at a rate to cause the ether to gently reflux. After the magnesium had been completely consumed, 260.8 g of the imine compound of Embodiment 16 above in 800 ml of anhydrous tetrahydrofuran was added dropwise at a rate to maintain the solvents, gently refluxing. The reaction mixture was stirred at 40° C. for 1 hour and 106.8 ml of methyl iodide was added dropwise at 10° C. The reaction mixture sat at room temperature overnight. The crude mixture was diluted with 2 liters of water and extracted thrice with 700 ml of ether. The Mg(OH)$_2$ was removed by celite filtration. The combined ether extracts were washed with 600 ml of saturated sodium chloride solution, dried (MgSO$_4$) and stripped on a rotary evaporator to leave 230.3 g of a yellow oil. This oil was vacuum distilled at 8–10 mm Hg to give four fractions of yellow oil as follows: 60.8 g at 63°–69° C., 40.6 g at 69°–70° C., 56.5 g at 71°–73° C. and 19.95 g at 73° C. The first three fractions contained the desired product.

EMBODIMENT 18

3,4-Dihydro-2-methyl-2H-pyran-2-carboxaldehyde

To a stirred solution of 17.0 g of acetice acid in 400 ml of water cooled to 15° C. was added 51.4 g of the imine compound of Embodiment 17 above while maintaining the temperature between 15°–25° C. by the rate of addition. After stirring for 1½ hours, the solution was saturated with sodium chloride and extracted thrice with 400 ml of diethyl ether. The combined ether extracts were washed with 300 ml of saturated sodium bicarbonate solution and 300 ml of saturated sodium chloride solution, dried (MgSO$_4$) and stripped on a rotary evaporator to leave 36.5 g of a colorless oil. This oil combined with oil from a similar preparation was Kugelrohr distilled at 35 mm Hg to give 31.65 g of the desired product as a colorless oil collected at 68°–75° C.

EMBODIMENT 19

3,4-Dihydro-2-methyl-2H-pyran-2-methanol

A solution of 5.9 g of sodium borohydride in 300 ml of 2:1 ethanol/water solvent was stirred vigorously while 29.9 g of the aldehyde of Embodiment 18 above was added dropwise at 25°–35° C., maintained by an ice bath. The reaction mixture was stirred at room temperature for 1 hour and then 35.2 ml of acetone was added dropwise at 25°–30° C. The resulting mixture was diluted with 300 ml of saturated aqueous potassium carbonate. The product was extracted four times with 900 ml of diethyl ether and the combined organic extracts were washed with 500 ml of saturated sodium chloride, dried (Na$_2$SO$_4$) and stripped on a rotary evaporator to leave 27.3 g of a pale yellow oil. This oil was Kugelrohr distilled at 2.2 mm Hg to give 23.7 g of the desired product collected at 85°–90° C.

EMBODIMENT 20

3,4,5,6-Tetrahydro-2-methyl-2H-pyran-2-methanol

A solution of 23.7 g of the alcohol of Embodiment 19 above in 200 ml of anhydrous ethanol and 2.4 g of 5% palladium on carbon was reacted in a 500 ml Parr Shaker apparatus under 55 psi hydrogen for 8 hours. The catalyst was removed from the reaction by filtration through a bed of celite. The solvents were stripped to leave 25.7 g of a colorless oil, which was Kugelrohr distilled at 1.9 mm Hg to give 21.3 g of the desired product collected at 60°–66° C.

EMBODIMENT 21

(3,4,5,6-Tetrahydro-2-methyl-2H-pyran-2-yl)methyl 4-Methylbenzensulfonate

To a solution of 50% sodium hydride (hexane washed), suspended in 20 ml of anhydrous tetrahydrofuran under nitrogen was added dropwise a solution of 5.0 g of the alcohol of Embodiment 20 above in 30 ml anhydrous tetrahydrofuran while cooling by an ice bath to 25°–35° C. The reaction mixture was refluxed for 1 hour, turning from grey to opaque white. A total of 8.9 g of recrystallized tosyl chloride was added portionwise at 10°–20° C. The reaction mixture was stirred at room temperature for three days. The reaction was quenched with 200 ml of water, extracted thrice with 100 ml of methylene chloride and the combined organic extracts were washed with 100 ml of 5% sodium hydroxide solution and 100 ml of saturated sodium chloride solution, dried (MgSO$_4$) and stripped on a rotary evaporator to leave 12.0 g of a thick yellow oil, which was flashed on a silica gel column using 1:5 diethyl ether/hexane as solvent. Two fractions were collected as follows: 1.50 g of colorless oil, R$_f$ 0.16 (ether/hexane 1:3) and 7.30 g of the desired product as a colorless oil, R$_f$ 0.11.

EMBODIMENT 22

(±)-2-exo-(3,4,5,6-Tetrahydro-2-methyl-2H-pyran-2-yl)-mthoxy)-1-methyl-4-(1-methylethyl)-7-oxabicyclo[2.2.1]-heptane A solution of 1.70 g of (±)-2-exo-hydroxy-1-methyl-4-(1-methylethyl)-7-oxabicyclo[2.2.1]heptane of Embodiment 2 above in 15 ml of dimethylacetamide was added dropwise to a suspension of 0.50 ml of sodium hydride (hexane washed) in 25 ml of dimethylacetamide. The reaction mixture was stirred at 45° C. for 1 hour, after which a solution of 2.75 g of the tosylate of Embodiment 21 above in 20 ml of dimethylacetamide was added dropwise. The reaction mixture was stirred for 3 days and then heated to 130° C. for 1 day. Another 0.50 g of sodium hydride was added and the reaction mixture was stirred at 130° C. for 6 hours. The reaction mixture was diluted with 200 ml of water, acidified to pH 7.0 with 6N hydrochloric acid and extracted four times with 200 ml of methylene chloride. The combined organic phases were washed with 350 ml of saturated sodium chloride, dried (MgSO$_4$) and stripped on a rotary evaporator to leave 20.0 g of a pale orange oil. The oil was flashed on a silica gel column using 1:2 diethyl ether/hexane solvent to give two fractions as follows: 300 mg of the desired product, R$_f$=0.29 (ether/hexane 1:2) and 200 mg of a fraction, R$_f$=0.23.

EMBODIMENT 23

3,4,5,6-Tetrahydro-alpha,6-dimethyl-2H-pyran-2-methanol

A solution of 14.2 g of the ketone of Embodiment 5 above in 130 ml of ethanol was added dropwise with cooling to a vigorously stirred solution of 2.5 g of sodium borohydride in 200 ml of 1:2 ethanol/water solvent. After stirring at room temperature for 1½ hours, the reaction mixture was quenched with 14.6 ml of acetone. The resulting solution was diluted with cold saturated aqueous potassium carbonate and extracted four times with 200 ml of diethyl ether. The combined ether extracts were washed with 200 ml of saturated sodium chloride, dried (MgSO$_4$) and stripped on a rotary evaporator to leave 14.3 g of a colorless oil, which was Kugelrohr distilled at 7 mm Hg to give 12.6 g of the desired product as a colorless oil collected at 74° C.

EMBODIMENT 24

(3,4,5,6-Tetrahydro-alpha,6-dimethyl-2H-pyran-2-yl)-methyl Methanesulfonate

To a solution of 12.1 g of the alcohol of Embodiment 23 above in 125 ml of methylene chloride was added via syringe 17.5 ml of triethylamine at −10° C. followed by 7.2 ml of freshly distilled mesyl chloride via syringe at −10° to 10° C. The latter addition was exothermic and the reaction mixture was stirred for 3 days at room temperature. The resulting mixture was diluted with 40 ml of water to dissolve the solids. The phases were separated and the organic layer was washed successively with 40 ml of cold 6N hydrochloric acid, 40 ml of saturated sodium bicarbonate solution and 40 ml of saturated sodium chloride solution, dried (MgSO$_4$) and stripped on a rotary evaporator to leave 18.3 g of a pale yellow oil, which was Kugelrohr distilled at 0.02 mm Hg to give 25.2 g of the desired product as a colorless oil collected at 95°-100° C.

EMBODIMENT 25

(±)-2-exo-((3,4,5,6-Tetrahydro-alpha,6-dimethyl-2H-pyran-2-yl)methoxy)-1-methyl-4-(1-methylethyl)-7-oxabicyclo[2.2.1]heptane A solution of 6.8 g of the alcohol of Embodiment 2 above, in 30 ml of dimethylacetamide was added dropwise to a solution of 1.98 g of sodium hydride (hexane washed) in 40 ml of dimethylacetamide. The opaque reaction mixture was heated at 67°-80° C. until a clear orange solution remained and 8.9 g of the mesylate of Embodiment 24 above in 30 ml of dimethylacetamide was added dropwise. The solution was stirred at 55°-70° C. for 5 days. The reaction mixture was diluted with 300 ml of water and extracted thrice with 200 ml of ethyl acetate. The combined organic extracts were washed with 200 ml of saturated sodium chloride solution, dried (MgSO$_4$) and stripped by water aspiration followed by high vacuum at 55° C. to leave 11.0 g of an orange oil, which was flashed on a silica gel column using 1:10 hexane/ethyl acetate as solvent to give two fractions as follows: 0.20 g of the desired product as a colorless oil, R$_f$=0.33 (1:8 ethyl acetate/hexane) and 3.54 g of a colorless oil, R$_f$=0.22.

EMBODIMENT 26

3,4-Dihydro-2H-pyran-2-methanol

A solution of 11.2 g of acrolein dimer in 12 ml of ethanol was added dropwise to a stirred solution of 2.47 g of sodium borohydride in 35 ml of 2:1 ethanol/water solvent, ice bath cooled to 20° C. After stirring at room temperature for 1½ hours, 14.6 ml of acetone was added. The reaction mixture was stirred for an additional 5 min, then diluted with 110 ml of saturated aqueous potassium carbonate. The product was extracted thrice with 250 ml of diethyl ether. The combined ether extracts were washed with 200 ml of saturated sodium chloride solution, dried (Na$_2$SO$_4$) and stripped on a rotary evaporator at 25° C. to leave 15.2 g of a pale yellow oil, which was Kugelrohr distilled at 4.2 mm Hg to give 10.9 g of a colorless oil collected at 65° C., using base-washed glassware.

EMBODIMENT 27

(3,4-Dihydro-2H-pyran-2-yl)methyl 4-Methylbenzenesulfonate

A solution of 5.25 g of the alcohol of Embodiment 26 above in 5 ml of anhydrous tetrahydrofuran was added dropwise to a solution of 2.65 g of sodium hydride (hexane washed) in 50 ml of anhydrous tetrahydrofuran. The reaction mixture was stirred at reflux for 1 hour and 10.55 g of recrystallized tosyl chloride was added portionwise at −5° C. to 0° C. The addition was exothermic, with foaming, and the resulting opaque mixture was stirred overnight. The ether was stripped off on a rotary evaporator to leave a purplish-white solid. This solid was dissolved in 500 ml of 1:1 ether/water solvent, the resulting phases were separated and the organic layer was washed twice with 200 ml of cold 10% sodium hydroxide solution and 100 ml of saturated sodium chloride solution, dried (Na$_2$SO$_4$) and stripped on a rotary evaporator to leave 10.6 g of a thick yellow oil-wet solid, which was recrystallized from 125 ml of ether/hexane to give 9.8 g of the desired product as a white solid, m.p. 45°-46° C.

EMBODIMENT 28

(±)-2-exo-((3,4-Dihydro-2H-pyran-2-yl)methoxy)-1-methyl-4-(1-methylethyl)-7-oxabicyclo[2.2.1]heptane To a solution of 0.86 g of 50% sodium hydride (pentane washed) in 25 ml of dry dimethylformamide was added portionwise 2.55 g of the alcohol of Embodiment 2 above. Some foaming occurred and the reaction mixture was heated to 70° C. for 1 hour. Then 4.82 g of the tosylate of Embodiment 27 above in 25 ml of dimethylformamide was added dropwise at 25°-35° C. The reaction mixture was heated to 55° C. for 2 hours and then stirred at room temperature for 3 days. Another 1.0 g of the tosylate was added and the mixture stirred was quenched in 200 ml of water and extracted 4 times with 150 ml of ether. The combined ether extracts were washed with 200 ml of saturated sodium chloride, dried (MgSO$_4$) and stripped on a rotary evaporator to leave 7.5 g of an orange oil, which was flashed on a silica gel column using 1:3 ether/hexane as solvent to give two fractions, the first being 0.10 g of the desired product as a colorless oil.

EMBODIMENT 29

(±)-2-exo-((3,4,5,6-Tetrahydro-5-hydroxy-2H-pyran-2-yl)methoxy)-1-methyl-4-(1-methylethyl)-7-oxabicyclo-[2.2.1]heptane A dry 200 ml 3-necked roundbottom flask was equipped with a septum cap, a nitrogen inlet, magnetic stirrer and thermometer and then charged with 36 ml of anhydrous tetrahydrofuran followed by 15.65 g of the ether of Embodiment 28 above, and the resulting solution was cooled to 0° C. While maintaining the internal temperature of the solution below 11° C., 20.7 ml of borane in tetrahydrofuran was added dropwise over 15 minutes. The reaction mixture was stirred at 0° C. for 3 hours, then stirred at room temperature for 2 hours, heated at 35° C. with the exothermic addition to 45° C. of 10.6 ml of 3N sodium hydroxide, added over 5 minutes followed by the exothermic addition to 60° C. of 7.1 g of hydrogen peroxide, added over 10 minutes. The reaction mixture was stirred at room temperature for 45 minutes and then 100 ml of saturated sodium chloride was added. The reaction mixture was stirred for 5 minutes and the resulting layers were separated. The aqueous layer was extracted thrice with 150 ml of diethyl ether, the ether layers were combined, dried (brine, MgSO$_4$), filtered and stripped to give an oil, which was chromatographed using 60% ethyl acetate in hexane as solvent. Fractions 32-50 gave 5.24 g of the desired alcohol as the equitorial isomer A, and fractions 72-83 gave 1.5 g of the desired alcohol of the equitorial/axial isomer B.

EMBODIMENT 30

(±)-2-exo-(3,4,5,6-Tetrahydro-5-oxo-2H-pyran-2-yl)-methoxy)-1-methyl-4-(1-methylethyl)-7-oxabicyclo[2.2.1]heptane A 200 ml 3-necked roundbottom flask equipped with a stirrer, thermometer, septum cap, N$_2$ inlet and 60 ml addition funnel was dried under N$_2$ and charged with 53 ml of anhydrous methylene chloride and oxalyl chloride and cooled to −50° C. A mixture of anhydrous dimethyl sulfoxide in 13.4 ml of methylene chloride was added over 5-10 minutes and the reaction mixture stirred for 10 minutes. A mixture of 3.15 g of the alcohol isomers of Embodiments 29A and 29B above in 15 ml of methylene chloride at −50° C. was added over 10 minutes and the resulting reaction mixture was stirred for 20 minutes at −50° C. A white, milky precipitate formed. Triethylamine was added over 15 minutes at −50° C., resulting in an exotherm to −20° C. and smoke formation above the reaction mixture. The reaction mixture was stirred at −50° C. to −60° C. for 2 hours, then 70 ml of water was added and the reaction mixture was stirred for 10 minutes at room temperature. The resulting phases were separated and the aqueous phase was extracted thrice with 100 ml of methylene chloride; these extracts were dried (brine, MgSO$_4$), filtered and stripped to give 7.0 g of a yellow oil, which was dried in vacuo overnight.

EMBODIMENT 31

(±)-2-exo-((3,4,5,6-Tetrahydro-5-methylene-2H-pyran-2-yl)methoxy)-1-methyl-4-(1-methylethyl)-7-oxabicyclo[2.2.1]heptane A 1 liter 3-necked roundbottom flask equipped with a stirrer, thermometer, N$_2$ inlet and septum cap was dried and charged with 1.66 g of sodium hydride (pentane washed) followed by syringe addition of dimethyl sulfoxide. The reaction mixture was heated to 65°-70° C. for 1 hour until gas evolution ceased. The resulting greenish emulsion was cooled to 0° C. and 9.5 g of methyl triphenyl phosphonium bromide in 35 ml of warm dimethyl sulfoxide was added in one portion. The reaction was exothermic to 10° C. and the mixture was stirred for 10 minutes at room temperature. A solution of 6.48 g of the ketone of Embodiment 30 above in 115 ml of anhydrous tetrahydrofuran was added as one portion, followed immediately by 500 ml of tetrahydrofuran. The reaction mixture was heated at 50° C., stirred overnight and quenched with 300 ml of ice water followed by 400 ml of pentane while vigorously stirring. After 10 minutes, the layers were separated, the aqueous layer extracted 4 times with 300 ml of pentane and the pentane layers dried (brine, MgSO$_4$), filtered and stripped to an oily solid. This solid was taken up in ether, washed thrice with 100 ml of water, dried and stripped to an oil, which was chromatographed using 25% ethyl acetate in hexane as solvent. The collected fraction was stripped and bulb-to-bulb distilled at 100°-108° C. to give 4.08 g of the desired product as a pale yellow oil.

EMBODIMENT 2

(±)-2-exo-((3,4,5,6-Tetrahydro-5-methyl-2H-pyran-2-yl)-methoxy)-1-methyl-4-(1-methylethyl)-7-oxabicyclo-[2.2.2]heptane A 500 ml Parr bottle was dried under argon and, when cool, charged with 65 ml of anhydrous ethyl acetate. This solvent was degassed for 10 minutes and then 650 mg of platinum oxide was added in one portion followed by 2.9 g of the ether of Embodiment 31 above in 5 ml of ethyl acetate. The bottle was placed in a Parr shaker and charged with hydrogen at 50 psi for 2½ hours. The reaction mixture was filtered through celite and washed several times with ethyl acetate. The resulting yellow solution was stripped and the residue chromatographed using 15% ethyl acetate in hexane as eluent to give the desired fraction, which was stripped to give 2.35 g of the desired product.

EMBODIMENT 33

(±)-2-exo-((3,4,5,6-Tetrahydro-5-methoxy-2H-pyran-2-yl)-methoxy)-1-methyl-4-(1-methylethyl)-7-oxabicyclo[2.2.1]heptane To a suspension of 0.24 g of 50% sodium hydride (pentane washed) in 5 ml of anhydrous tetrahydrofuran was added dropwise at 10°-20° C. a solution of 1.28 g of the alcohol of Embodiment 29 above in 7 ml of anhydrous tetrahydrofuran. Gas evolved during the addition and the reaction mixture was stirred at 25° C. for 1 hour followed by the syringe addition of 0.768 g of methyl iodide. The reaction mixture was stirred at room temperature overnight, then diluted with 30 ml of water, extracted 4 times with 30 ml of methylene chloride, the combined organic layers were washed with 50 ml of saturated sodium chloride solution, dried (MgSO$_4$) and stripped on a rotary evaporator to leave 1.30 g of a viscous, colorless oil, which was flash chromatographed on silica gel using 1:2 ether/hexane as solvent to give 1.0 g of the desired product as a viscous, colorless oil.

EMBODIMENT 34

(±)-1,3,3-Trimethyl-2-oxabicyclo[2.2.2]octan-6-exo-ol

To a stirred solution of 30.8 g of (±)-alpha-terpineol in 300 ml of methylene chloride kept below 10° C. was added portionwise 43.0 g of 85% m-chloroperbenzoic acid. After 3 hours, 0.5 g of p-toluenesulfonic acid was added, and reaction was allowed to continue overnight at 5°–15° C. The resulting reaction mixture was washed with aqueous potassium carbonate, dried, and Claisen distilled to give 14.3 g of product b.p. 68°–75° C. (1 mm) and 12.6 of by-product, b.p. 75°–85° C. (1 mm). Redistillation of the product through a micro Vigreaux column gave 7.9 g of 90–95% purity product, b.p. 85°–95° C. (3 mm). A heart cut was recrystallized from pentane to give the product with m.p. 64°–66° C.

EMBODIMENT 35

(±)-alpha-Terpineol

Following a procedure described in Matsubara, et al., Chem. Abstr., 84:165069b (1976), 64.5 g of dichloroacetic acid was added dropwise over 20 minutes at 5°–6° C. to a magnetically stirred mixture of 68.0 g of (+)-alpha-pinene ([alpha]$_D$+47.1°) and 9.0 g of water. After stirring overnight at 5°–30° C. (ice allowed to melt slowly), the mixture was extracted with 400 ml of methylene chloride. The extract was washed successively with water, aqueous potassium carbonate solution and water, dried and Claisen distilled at 4 mm to give 11.2 g of forecut, b.p. 40°–71° C. and 47.5 g of the desired (+)-alpha-terpineol, b.p. 71°–83° C. Redistillation through a micro Vigreaux column gave 40.5 g of (+)-alpha-terpineol with [alpha]$_D$+79.3° (CHCl$_3$), b.p. 58°–60° C. (1 mm).

EMBODIMENT 36

(+)-1,3,3-Trimethyl-2-oxabicyclo[2.2.2]octan-6-exo-ol

To a stirred solution of 112 g of m-chloroperbenzoic acid in 500 ml of methylene chloride was added dropwise at 30°–35° over 1.5 hours a solution of 77 g (+)-alpha-terpineol ([alpha]$_D$+77.1° (CHCl$_3$)) in 75 ml of methylene chloride. After stirring overnight at 25° C., the mixture was washed successively with one-fourth saturated potassium carbonate, saturated sodium sulfite and 2N sodium hydroxide. The dried methylene chloride solution was vacuum-concentrated (water aspirator) at 90° C. to a residue of 73 g. This was distilled through a micro Vigreaux column at 5 mm to give 42.3 of crude product, b.p. 95°–107° C. Recrystallization from 150 ml of pentane at −10° C. gave 10.2 g of product, m.p. 90°–93° C.; [alpha]$_D$+24.2° (CHCl$_3$).

EMBODIMENT 37

(+)-1,3,3-Trimethyl-2-oxabicyclo[2.2.2]octan-6-one

To a stirred solution of 8.7 g of (+)-1,3,3-trimethyl-2-oxabicyclo[2.2.2]octan-6-exo-ol in 250 ml of acetone was added 60 ml of water followed by 21.0 g of N-bromoacetamide. When the latter had dissolved within 1 minute, the reaction mixture was immediately cooled to less than 10° C. and stored overnight in a refrigerator. The orange-colored solution was poured with stirring into 200 ml of water containing 38 g of sodium sulfite. After vacuum concentration at 50°–55° C. to remove most of the acetone, the residue was treated with solid ammonium sulfate and extracted with four 125 ml portions of methylene chloride. The combined methylene chloride extract was washed with 100 ml of water, dried, and concentrated to a residue of 7.6 g. Recrystallization from 200 ml of pentane gave 6.0 g of product, m.p. 40°–48° C., [alpha]$_D$+74.3° (CHCl$_3$).

EMBODIMENT 38

(+)-1,3,3-Trimethyl-6-endo-(3,4,5,6-tetrahydro-2H-pyran-2-yl)methoxy)-2-oxabicyclo[2.2.2]octane Following procedures similar to those described in Embodiment 4 above, the desired product is prepared by reducing (+)-1,3,3-trimethyl-2-oxabicyclo[2.2.2]octane-6-one with sodium borohydride followed by treating the resulting alcohol with the mesylate of Embodiment 3 above in the presence of sodium hydride.

EMBODIMENT 39

1-Acetyl-2-(2-propen-2-yl)cyclopropanecarboxylic Acid, Ethyl Ester

Ethyl acetoacetate (125.8 g) in 400 ml of toluene was added dropwise to a suspension of sodium hydride (68.3 g of a 60% oil dispersion washed with pentane) in 1 L of toluene under an N$_2$ blanket at −6° C. to 2° C. After 20 minutes, 1,4-dibromo-2-methyl-2-butene (220.6 g) in 300 ml of toluene was added dropwise at −2° C. to 0° C. The reaction mixture was allowed to warm to ambient temperature and after 22 hours, was diluted with water and extracted with ethyl acetate (thrice). The combined organic extracts were washed with water, brine, dried and concentrated in vacuuo. GLC of the crude material indicated 77% of the two desired isomers. The isomers were separated by flash chromatography using 7.5% ethyl acetate in hexane, giving ca 90% pure isomers.

In one instance the initial work-up from a second similar experiment was separated on a preparative HPLC (silica gel hexane-EtOAc gradient). A set of fractions was distilled to give the lower R$_f$ isomer as a colorless liquid, b.p. 50° C. at 0.08 mmHg.

A less polar set of fractions was distilled to give the higher R$_f$ isomer as a colorless liquid, b.p. 50° C. at 0.08 mm.

EMBODIMENT 40

3-Methyl-1-(1-oxoethyl)-3-cyclopentene-1-carboxylic Acid, Ethyl Ester

The product mixture of isomers from Embodiment 39 above was passed neat under nitrogen at about 40 drops per minute through a pyrolysis column packed with glass helicies (previously washed with ammonium hydroxide, acetone and hexane) and heated at 500° C. The pyrolysate was collected in heptane cooled by a dry ice bath. The heptane was removed in vacuuo and the residue was dissolved in diethyl ether, washed twice with 5% sodium hydroxide, brine, dried (Na$_2$SO$_4$), concentrated in vacuuo, and kugelrohr distilled at 80° C. (0.08 mm) to give a crude product. This crude pyrolysis product was separated twice on a silica gel preparative HPLC with ethyl acetate-hexane as eluent. The major component was distilled to give the desired product as a colorless liquid, b.p. 85° C. (1.3 mm).

EMBODIMENT 41

1-(1-Methyl-1-cyclopenten-4-yl)ethanone

A solution of potassium hydroxide (4.03 g) in water (20 ml) was added in one portion to a solution of 1.00 g the product of Embodiment 40 above in MeOH (5 ml). The reaction was warmed to reflux for 20 minutes, diluted with water and extracted with diethyl ether three times. The combined extracts were washed with brine, dried (Na$_2$SO$_4$) and concentrated in vacuo. The crude material was vacuum distilled to about 90% purity and carried to the next step.

In another similar experiment the distillation gave the desired product, b.p. 80° C. (27 mm) as a colorless liquid.

EMBODIMENT 42 alpha,alpha,3-Trimethyl-3-cyclopentene-1-methanol

A solution of the crude product of Embodiment 41 above in 40 ml of tetrahydrofuran was added to 24 ml methylmagnesium bromide in diethyl ether at −50° C. to −10° C. under nitrogen. The reaction mixture was kept at −20° C., and after 2 hours was diluted with cold saturated ammonium chloride. The solution was extracted with diethyl ether three times, and the combined extracts were washed with brine, dried (MgSO$_4$) and concentrated in vacuo. The residue was separated by flash silica gel chromatography using about 2.4 L of a 40/2/8 hexane/tetrahydrofuran/ethyl acetate mixture. A small portion of the fraction containing the desired product was distilled to give 0.26 g of the desired product as a colorless liquid, b.p. 50° C. (0.6 mm).

EMBODIMENT 43

1,3,3-Trimethyl-B 2-oxabicyclo[2.2.1]heptan-6-exo-ol

A solution of 0.26 g of the product of Embodiment 42 above in 4 ml chloroform was added dropwise to refluxing 40% peracetic acid under a nitrogen blanket. After one-half hour, the solution was cooled, diluted with methylene chloride, washed with 25% potassium carbonate, saturated sodium chloride, dried (MgSO$_4$) and concentrated in vacuo. The mixture was separated on a silica gel preparative HPLC using hexaneethyl acetate as eluent to give 0.44 g of the desired product as a yellow liquid.

EMBODIMENT 44

1,3,3-Trimethyl-2-oxabicyclo[2.2.1]heptan-6-one

To a solution of 3.96 g of oxalyl chloride in 36 ml of methylene chloride was added a solution of 5.11 g of dimethyl sulfoxide in 12 ml of methylene chloride at −60° C. to −70° C. under nitrogen. After 10 minutes, 4.44 g of crude 1,3,3-trimethyl-2-oxabicyclo[2.2.1]heptan-6-exo-ol (Embodiment 43) in 12 ml methylene chloride was added dropwise at −60° C. After 15 minutes, 14.3 g of triethylamine was added at −70° C. to −50° C. The reaction was allowed to warm to −20° and diluted with water. The CH$_2$Cl$_2$ phase was separated, and the aqueous phase was saturated with sodium chloride and extracted twice with methylene chloride. The combined organic phases were dried (MgSO$_4$) and concentrated in vacuo. The residue was separated by silica gel flash chromatography using 2 L of 40/2/8 hexane/tetrahydrofuran/ethyl acetate and 2 L of 33/2/15 hexane/tetrahydrofuran/ethyl acetate mixture as eluents. One set of fractions gave 2.08 g of the desired product as a yellow liquid.

EMBODIMENT 45 endo-1,3,3-Trimethyl-2-oxabicyclo[2.2.1]heptan-6-ol

To a solution of 16 ml of lithium tri-sec-butylborohydride in tetrahydrofuran was added 2.05 g of the ketone of Embodiment 44 in 10 ml dry tetrahydrofuran at −70° C. to −62° C. under nitrogen. The reaction mixture was stirred for 1 hour at −70° C. and then 1 hour at ambient temperature. To the mixture was successively added 1.1 ml of water, 2.4 ml of ethanol, 13.3 ml of 10% sodium hydroxide and 5.8 ml of 30% hydrogen peroxide. After 1 hour, the reaction mixture was saturated with potassium carbonate and extracted with diethyl ether three times. The combined extracts were dried (MgSO$_4$) and concentrated in vacuo to give 1.56 g of the desired product as a yellow liquid.

EMBODIMENT 46

1,3,3-Trimethyl-6-endo-((3,4,5,6-tetrahydro-2H-pyran-2-yl)methoxy)-2-oxabicyclo[2.2.1]heptane Following procedures similar to those described in Embodiment 4, the desired product is prepared by treating endo-1,3,3-trimethyl-2-oxabicyclo[2.2.1]heptan-6-ol with the mesylate of Embodiment 3 above.

The compounds of the Invention have been found useful for influencing plant growth and controlling the growth of unwanted plants, being particularly active with respect to grassy weeds and some broadleafed plants. For example, the compounds can change plant morphology; depress the growth of plants, such as broadleafed weeds; inhibit germination; or totally or selectively kill plants depending on the amount used. As herbicides, they appear to be more effective when applied preemergence or pre-plant incorporated (applied to the soil before the seeds have sprouted) than when applied postemergence (applied to the foliage). The compounds of the invention show selectivity to crops, such as cotton and sugar beets, and, particularly good control of grassy weeds, such as barnyard grass, yellow foxtail, downy brome, goosegrass, Johnson grass, yellow nutsedge, and the like, and certain broadleaf weeds, such as cocklebur, velvetleaf, and the like, especially in preemergence application.

Protection of a locus or area from undesireable plants is effected by applying a Compound of the Invention, ordinarily a composition of one of the aforementioned types, to the soil in which the plant is growing or in which the seeds are present or to plant and foliage. The Compounds of the Invention, of course, are applied in amounts sufficient to exert the desired action.

For application, the compound of Formula 1 ordinarily is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula 1.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; ketones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or wetting agent; it may be non-ionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3–10% by weight of a dispersing agent, 2–15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.152 mm), and may be manufactured by agglomeration of impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additives such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be disolved in the carrier to assist in preventing sedimentation or as antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3–7% by weight of a blend of surfactants, which act as wetting, dispersing, suspending and binding agents, and 1–3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula I as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula 1, ordinarily in a composition of one of the aforementioned types, to soil in which the seeds of the unwanted plants are present, or the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected from 0.1 to 10.0 kg per hectare of the compound of Formula 1 will be satisfactory.

EXAMPLES OF ACTIVITY WITH RESPECT TO PLANTS

In the following examples, the species of plants that were tested were:

Barnyardgrass (watercress)—*Echinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnson grass—*Sorghum halepense*
Morningglory—*Ipomoea purpurea* L. (Roth)

TEST PROCEDURES

The preemergence (soil) herbicidal activity of compounds of Formula 1 was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3-4 | Observable damage |
| 1-2 | Plant slightly affected, possibly by the chemical, possibly due to biological variability |
| 0 | No visible effect |

The postemergence (foliar) herbicidal activity of compounds of Formula I was eveluated by spraying 10-day-old large crabgrass plants, 13-day-old pigweed plants, 6-day-old Johnsongrass plants, 9-day-old velvetleaf plants, 9-day-old yellow foxtail plants and either 9-day-old sicklepod plants or 5-day-old morningglory plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days, when the effect of the test compound was evaluated visually, the results being rated on the 0 to 9 scale described above.

Results of the preemergence and postmergence herbicidal activity tests are set forth in Table I.

TABLE I

HERBICIDAL ACTIVITY

| Compound | Preemergence | | | | | | | Postemergence | | | | | | |
|---|---|---|---|---|---|---|---|---|---|---|---|---|---|---|
| | Barnyardgrass | Garden Cress | Downy Brome | Velvetleaf | Yellow Foxtail | Sicklepod | Morningglory | Crabgrass | Pigweed | Johnsongrass | Velvetleaf | Yellow Foxtail | Sicklepod | Morningglory |
| 4 | 9 | 7 | 9 | 7 | 9 | 6 | — | 7 | 4 | 3 | 4 | 6 | 3 | — |
| 9 | 9 | 7 | 7 | 7 | 6 | — | 6 | 2 | 3 | 0 | 2 | 0 | — | 2 |
| 15 | 9 | 7 | 9 | 6 | 8 | — | 2 | 5 | 3 | 0 | 2 | 1 | — | 0 |
| 22 | 9 | 7 | 8 | 4 | 8 | — | 3 | 0 | 0 | 0 | 0 | 0 | — | 0 |
| 25 | 9 | 6 | 3 | 5 | 5 | — | 2 | 0 | 0 | 0 | 0 | 0 | — | 0 |
| 29A | 9 | 2 | 6 | 2 | 4 | — | 2 | 0 | 3 | 0 | 2 | 0 | — | 2 |
| 29B | 9 | 0 | 6 | 0 | 5 | — | 0 | 0 | 0 | 0 | 0 | 0 | — | 0 |
| 28 | 8 | 7 | 9 | 3 | 3 | — | 7 | 6 | 2 | 0 | 2 | 0 | — | 0 |
| 30 | 8 | 2 | 4 | 0 | 4 | — | 0 | 0 | 0 | 0 | 0 | 0 | — | 0 |
| 32 | | | | | | | | | | | | | | |
| 33 | | | | | | | | | | | | | | |

— means no test.

In the following examples, the species of plants that were tested were:

Barnyardgrass
Downy Brome
Johnsongrass
Wild oats—*Avena fatua*
Yellow foxtail
Goose grass—*Eleusine indicia* L.
Yellow nutsedge—*Cyperus esculentus*
Cocklebur—*Xanthym pennsylvanicum*
Morningglory
Wild mustard—*Brassica kaber*
Redroot pigweed
Sicklepod
Velvetleaf

TEST PROCEDURES

The preemergence activity of the compound of Embodiment 4 was further determined with respect to certain common species of weeds, by spraying a formulation of the test compound on soil in small pots in which seeds of the plants had been sown. In each series of tests, the plants were grown in narrow trays and sprayed with the formulation. The results of the tests were evaluated on the basis of the 0–9 scale described with respect to the earlier tests. The average of the results of three separate tests on the these species of plants are reported in Table II.

TABLE II

| Compound of Embodiment 4, Rating of Effect at Indicated Dosage (lb/acre) | | |
|---|---|---|
| | Preemergence | |
| Plant Species | 0.25 | 1.0 |
| Barnyard Grass | 9 | 9 |
| Downey Brome | 9 | 9 |
| Johnsongrass | 9 | 9 |
| Wild Oats | 6 | 7 |
| Yellow Foxtail | 9 | 9 |
| Goose Grass | 9 | 9 |
| Yellow Nutsedge | 9 | 9 |
| Cocklebur | 9 | 8 |
| Morning Glory | 0 | 0 |
| Mustard | 1 | 5 |
| Pigweed | 2 | 6 |
| Sicklepod | 0 | 3 |
| Velvetleaf | 5 | 7 |

What is claimed is:

1. A compound of the formula

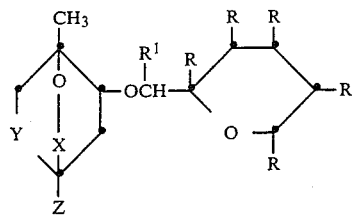

where X is a bond or $-C(CH_3)_2-$; Y is a single bond or $-CH_2-$ with the proviso that both X and Y are not a single bond; Z is a hydrogen atom or, an alkyl group containing 1 to 4 carbon atoms; each R independently is a hydrogen atom, a hydroxy group, an oxo group, a methylene group, or an alkyl or alkoxy group containing from 1 to 6 carbon atoms or one pair of adjacent R groups from a carbon-carbon bond; and $R^1$ is a hydrogen atom or an alkyl group containing from 1 to 6 carbon atoms.

2. A compound according to claim 1 wherein each R independently is a hydrogen atom, an alkyl or alkoxy group containing 1 or 2 carbon atoms and $R^1$ is a hydrogen atom or a methyl group.

3. A compound according to claim 2 wherein each R independently is a hydrogen atom or a methyl group and $R^1$ is a hydrogen atom.

4. A compound according to claim 1 wherein (1) X is a single bond, Y is $-CH_2-$, Z is a hydrogen atom or (1-methylethyl) group or (2) X is $-C(CH_3)_2-$, and Z is a hydrogen atom.

5. A compound according to claim 4 wherein X is a single bond, and Z is (1-methylethyl).

6. A compound according to claim 5 wherein each R is a hydrogen atom.

7. A compound according to claim 6 wherein the (3,4,5,6-tetrahydro-2H-pyran-2-yl)methoxy group is exo to the oyxgen bridge.

8. A herbicidal or plant growth regulating composition comprising a herbicidally effective amount of a compound according to claim 1 and at least one carrier or surface-active agent.

9. A method of controlling undesirable plant growth at a locus comprises applying to the locus or the plants an effective amount to control undesirable plant growth of a compound according to claim 1.

10. A method according to claim 9 wherein the control is herbicidal.

* * * * *